United States Patent [19]

Ito et al.

[11] 4,237,074

[45] Dec. 2, 1980

[54] ISOMERIZATION OF DICHLOROBUTENES

[75] Inventors: Higashi Ito; Seiichi Watanabe, both of Ohmimachi, Japan

[73] Assignee: Denkyi Kagaku Kohyo Kabushiki Kaisha, Tokyo, Japan

[21] Appl. No.: 63,257

[22] Filed: Aug. 2, 1979

Related U.S. Application Data

[63] Continuation-in-part of Ser. No. 941,685, Sep. 12, 1978, abandoned.

[30] Foreign Application Priority Data

Sep. 30, 1977 [JP] Japan ................................. 52-116879
Sep. 30, 1977 [JP] Japan ................................. 52-116880

[51] Int. Cl.$^3$ ............................................. C07C 17/00
[52] U.S. Cl. ................................................... 570/236
[58] Field of Search ....................................... 260/654 R

[56] References Cited

U.S. PATENT DOCUMENTS

| 3,751,493 | 8/1973 | Capp et al. ....................... 260/654 R |
| 3,927,130 | 12/1975 | Kadowaki et al. ............... 260/654 R |

FOREIGN PATENT DOCUMENTS

| 723185 | 12/1965 | Canada ................................ 260/654 R |
| 798899 | 7/1958 | United Kingdom ................ 260/654 R |
| 1300430 | 12/1972 | United Kingdom ................ 260/654 R |
| 1327983 | 8/1973 | United Kingdom ................ 260/654 R |

Primary Examiner—Delbert E. Gantz
Assistant Examiner—Joseph A. Boska
Attorney, Agent, or Firm—Oblon, Fisher, Spivak, McClelland & Maier

[57] ABSTRACT 3,4-Dichlorobutene-1 and 1,4-dichlorobutene-2 are isomerized in the presence of a catalyst of a combination of a copper compound or copper metal and at least one additive from the group of 1,3-diphenylguanidine, di-o-tolylguanidine, glycine ethyl ester hydrochloride and 2-amino-4-chlorophenol.

5 Claims, No Drawings

4,237,074

ISOMERIZATION OF DICHLOROBUTENES

CROSS REFERENCE TO RELATED APPLICATIONS

This application is a continuation-in-part of application Ser. No. 941,685 filed Sept. 12, 1978, now abandoned.

BACKGROUND OF THE INVENTION

1. Field of the Invention

The present invention relates to an improved reaction for the isomerization between 3,4-dichlorobutene-1 and 1,4-dichlorobutene-2.

2. Description of the Prior Art

Heretofor it has been proposed to heat a dichlorobutene isomer in the presence of an isomerization catalyst of at least one metal salt of copper, iron, zinc or aluminum. However, these catalysts have relatively low catalytic activity. Therefore, it has been proposed to improve the activity of these catalysts by adding various auxiliary catalysts to the metal salts. For example, British Patent No. 798,889 proposes the addition of an organic amine to a copper salt, Japanese Unexamined Patent Publication No. 1514/1971 proposes the addition of an organic nitrile to cupric naphthenate, Japanese Unexamined Patent Publication No. 11560/1972 proposes the addition of an organic dihydroxy compound to a salt, Japanese Unexamined Patent Publication No. 18808/1972 proposes the addition of an aniline chlorinated derivative to a salt, and Japanese Patent Publication No. 42853/1973 proposes the addition of an amine hydrochloride to cuprous chloride.

U.S. Pat. No. 3,927,130 also shows a technique for effecting the isomerization of dichlorobutene starting materials in which a catalyst of a combination of a metal compound such as cupric sulfate, cupric acetate, ferric chloride, or the like or even copper metal and an amine salt such as the hydrochloride salt of triethylamine, diethylamine, or ethylenediamine is employed.

In some studies it has been found that large amounts of by-products having high boiling points as tar are produced when an amine is added to the catalyst, and satisfactory catalytic activity can not be achieved in low concentration of the known catalysts.

It has also been found that it is necessary to use an isomerization catalyst in the reaction which has high catalytic activity and which results in lower decomposition of dichlorobutene and fewer side-reactions which form by-products having high boiling points and which is not corrosive in reaction apparatus.

The decomposition of the dichlorobutene and the formation of tar by-products of high boiling points are problems which result in decreased yields of the desired dichlorobutene isomer product and in the clogging of the reaction apparatus which shortens the operable time frame of the reaction.

Normally catalyst concentration is increased in a reaction system to increase the degree of catalyst activity. On the other hand, from the point of view of economy and recovery of the waste catalyst, it is undesirable to use greater quantities of catalyst.

Canadian Patent 723,185 discloses a catalyst system which promotes isomerization reactions between 3,4-dichlorobutene-1 and 1,4-dichlorobutene-2 which consists of a combination of a cuprous salt and a halide solubilizing agent which can be a halide salt of an organic base such as morpholine hydrochloride, hexamethylenediamine dihydrochloride, hydroxylamine hydrochloride, piperidine hydrochloride or the like. However, the reaction is conducted in a water miscible organic solvent which can give rise to certain disadvantages.

SUMMARY OF THE INVENTION

Accordingly, one object of the present invention is to provide a method by which a desired dichlorobutene isomer can be obtained in high yield by the isomerization of dichlorobutenes in the presence of a catalyst of high catalytic activity at relatively low temperature while preventing side-reactions which produce tar by-products of high boiling points and while preventing the clogging of the reaction apparatus.

Another object of the present invention is to achieve a desired dichlorobutene isomer in high yield from a reaction which employs a catalyst in lower concentrations.

The foregoing and other objects of the present invention can be attained by conducting the isomerization reaction between 3,4-dichlorobutene-1 and 1,4-dichlorobutene-2 in the presence of a catalyst which is a combination of a copper compound or copper metal and at least one compound selected from the group of 1,3-diphenylguanidine, di-o-tolylguanidine, glycine ethyl ester hydrochloride and 2-amino-4-chlorophenol.

DETAILED DESCRIPTION OF THE PREFERRED EMBODIMENTS

The catalysts used in the isomerization reaction of the present invention have high catalytic activity at low concentrations in the dichlorobutene starting material. Moreover, the formation of tar or solid byproducts of high boiling points is significantly reduced and the reaction apparatus is not significantly corroded during reaction.

With regard to the concentration of the catalyst to the dichlorobutene reactant, the concentration of the copper compound usually ranges from 0.05 to 2 wt.%, especially 0.1 to 1 wt.% while the concentration of 1,3-diphenylguanidine, di-o-tolylguanidine, glycine ethyl ester hydrochloride and 2-amino-4-chlorophenol usually ranges from 0.05 to 4 wt.%, especially 0.15 to 2 wt.%.

When 1,3-diphenylguanidine or di-o-tolylguanidine is used, it is preferably to combine it with cuprous chloride (CuCl) and, the concentration of 1,3-diphenylguanidine and di-o-tolylguanidine is preferably in a range of 0.05 to 2 wt.% and especially 0.15 to 0.6 wt.%.

The copper compounds used as the metal containing component of the catalyst include, organic and inorganic copper compounds especially cuprous chloride, cupric naphthenate and cupric acetate. Metallic copper can also be used.

The reaction temperature for the isomerization reaction is usually in a range of 80° to 130° C., preferably 85° to 95° C. If the reaction temperature is lower, the reaction velocity is less. On the other hand, if the reaction temperature is higher, the decomposition of dichlorobutene and the formation of by-products of high boiling point are increased.

The reaction pressure can be atmospheric pressure, or greater or less than atmospheric pressure.

The isomerization of the present invention can be carried out by a batch process or a continuous process in a distillation tower.

It is mostly preferred in an industrial operation to carry out the isomerization by filling the bottom of the distillation tower with the catalyst and discharging the desired dichlorobutene isomer as a distillate or as a discharged product.

The distillation is preferably carried out under a reduced pressure of 40 to 100 mmHg. (absolute) and the reaction is preferably carried out at the boiling point of the dichlorobutene.

If necessary, the reactor can be equipped with a distillation tower to recycle the dichlorobutene from the reactor to the bottom of the tower.

In the continuous process, it is necessary to discharge a part of the reaction mixture at the bottom of the tower in order to prevent an accumulation of by-products of high boiling points. In this case, the catalyst is lost so that it is preferably to add the catalyst in order to maintain a constant concentration of the catalyst.

Copending application (Attorney docket No. 91-030-0) relates to an isomerization catalyst system which is a combination of a copper metal containing component and piperidine hydrochloride.

Having generally described this invention, a further understanding can be obtained by reference to certain specific examples which are provided herein for purposes of illustration only and are not intended to be limiting unless otherwise specified.

EXAMPLES 1 TO 9

In a 300 ml four-necked flask equipped with a stirrer and a condenser, 250 ml of 1,4-dichlorobutene-2 or 3,4-dichlorobutene-1 was charged and heated with stirring. Cuprous chloride and either 1,3-diphenylguanidine or di-o-tolylguanidine as the catalyst components were simultaneously added to the specific temperature.

The reaction was continued for 60 minutes as the specific reaction temperature after the addition of the catalyst and then the reaction mixture was sampled and analyzed by gas chromatography.

The results of the experiments are shown in Tables 1 and 2. In Table 1, the results of the isomerization of 1,4-dichlorobutene-2 are shown and in Table 2, the results of the isomerizations of 3, 4-dichlorobutene-1 are shown. In the Tables, 3, 4-DCB designates 3, 4-dichlorobutene-1, and 1, 4-DCB designates 1, 4-dichlorobutene-2. The compositions of the dichlorobutenes used for the experiments are shown as the starting materials together with the catalyst. The concentration of the catalyst or the additive shown by weight is based on the dichlorobutenes.

In Tables 1 and 2, the catalytic components are shown by the following symbols.

Diphenyl Gua.: 1, 3-diphenylguanidine
Ditolyl Gua.: di-o-tolylguanidine

TABLE 1

Isomerization of 1, 4-dichlorobutene-2

| Exp. | Catalyst | Concentration of catalyst (wt. %) | Reaction Temp. (°C.) | Composition (wt. %) 3,4-DCB | cis-1,4-DCB | trans-1,4-DCB |
|---|---|---|---|---|---|---|
| — | Starting material dichlorobutene | — | — | 0.84 | 29.74 | 69.42 |
| 1 | CuCl | 0.10 | 85 | 10.15 | 28.17 | 61.68 |
|   | Diphenyl Gua. | 0.15 | | | | |
| 2 | CuCl | 0.15 | 90 | 14.27 | 26.78 | 58.95 |
|   | Diphenyl Gua. | 0.23 | | | | |
| 3 | CuCl | 0.20 | 90 | 16.46 | 26.50 | 57.04 |
|   | Diphenyl Gua. | 0.30 | | | | |
| 4 | CuCl | 0.30 | 95 | 18.76 | 25.02 | 56.22 |
|   | Diphenyl Gua. | 0.60 | | | | |
| 5 | CuCl | 0.10 | 90 | 10.40 | 27.80 | 61.80 |
|   | Ditolyl Gua. | 0.15 | | | | |
| 6 | CuCl | 0.15 | 90 | 12.01 | 27.50 | 60.49 |
|   | Ditolyl Gua. | 0.23 | | | | |

TABLE 2

Isomerization of 3, 4-dichlorobutene-1

| Exp. | Catalyst | Concentration of catalyst (wt.%) | Reaction temp. (°C.) | Composition (wt.%) 3,4-DCB | cis-1,4-DCB | trans-1,4-DCB |
|---|---|---|---|---|---|---|
| — | Starting material dichlorobutene | — | — | 99.86 | 0.04 | 0.10 |
| 7 | CuCl | 0.10 | 90 | 60.97 | 1.11 | 37.92 |
|   | Diphenyl Gua. | 0.15 | | | | |
| 8 | CuCl | 0.15 | 90 | 56.25 | 1.29 | 42.46 |
|   | Diphenyl Gua. | 0.25 | | | | |
| 9 | CuCl | 0.15 | 90 | 50.42 | 1.46 | 48.12 |
|   | Ditolyl Gua. | 0.23 | | | | |

EXAMPLES 10 TO 30

In a 300 ml four-necked flask equipped with a stirrer and a condenser, 250 ml of 1, 4-dichlorobutene-2 or 3, 4-dichlorobutene-1 was charged and heated with stirring. A copper compound and either piperidine hydrochloride, glycine ethyl ester hydrochloride or 2-amino-4-chlorophenol as the catalyst components were simultaneously added to the dichlorobutene while controlling the reaction temperature at a specific temperature. The reaction was continued for 60 minutes at the specific reaction temperature after the addition of the catalyst and then the reaction mixture was sampled and analyzed by gas chromatography.

The results of the experiments are shown in Tables 3 and 4.

In Table 3, the results of the isomerization of 1, 4-dichlorobutene-2 are shown and in Table 4 the results of the isomerization of 3, 4-dichlorobutene-1 are shown.

The cupric naphthenate catalyst component used in some experiments was a commercial product containing 10 wt.% of Cu.

In Tables 3 and 4, the catalyst components are defined by the following symbols.

Pip. HCl: piperdine hydrochloride
Ethyl Gly. HCl: glycine ethyl ester hydrochloride
Amino Cl Phenol: 2-amino-4-chlorophenol

TABLE 3

Isomerization of 1, 4-dichlorobutene-2

Invention:

| Exp. | Catalyst | Concentration of catalyst (wt. %) | Reaction temp. (°C.) | Composition (wt. %) 3,4-DCB | cis-1,4-DCB | trans-1,4-DCB |
|---|---|---|---|---|---|---|
| — | Starting material dichlorobutene | — | — | 0.84 | 29.74 | 69.42 |
| 10 | CuCl | 0.10 | 90 | 14.90 | 28.14 | 56.96 |
|  | Pip . HCl | 0.10 |  |  |  |  |
| 11 | CuCl | 0.15 | 90 | 17.75 | 27.40 | 54.85 |
|  | Pip . HCl | 0.15 |  |  |  |  |
| 12 | CuCl | 0.31 | 95 | 19.21 | 26.49 | 54.30 |
|  | Pip . HCl | 0.62 |  |  |  |  |
| 13 | Cupric naphthenate | 0.64 | 90 | 11.70 | 29.40 | 58.90 |
|  | Pip . HCl | 0.97 |  |  |  |  |
| 14 | Cupric acetate | 0.18 | 90 | 11.60 | 29.35 | 59.05 |
|  | Pip . HCl | 0.28 |  |  |  |  |
| 15 | CuCl | 0.10 | 90 | 13.45 | 28.44 | 58.11 |
|  | Ethyl Gly . HCl | 0.15 |  |  |  |  |
| 16 | CuCl | 0.31 | 95 | 18.15 | 23.80 | 58.05 |
|  | Ethyl Gly . HCl | 0.62 |  |  |  |  |
| 17 | Cupric naphthenate | 0.64 | 90 | 14.81 | 29.34 | 55.85 |
|  | Ethyl Gly . HCl | 0.97 |  |  |  |  |
| 18 | Cupric acetate | 0.18 | 90 | 12.03 | 29.04 | 58.93 |
|  | Ethyl Gly . HCl | 0.28 |  |  |  |  |
| 19 | CuCl | 0.31 | 95 | 18.11 | 26.24 | 55.65 |
|  | Amino Cl Phenol | 0.62 |  |  |  |  |
| 20 | Cupric naphthenate | 0.64 | 90 | 12.38 | 28.71 | 58.91 |
|  | Amino Cl Phenol | 0.97 |  |  |  |  |
| 21 | CuCl | 0.10 | 90 | 17.21 | 27.03 | 55.76 |
|  | Pip . HCl | 0.15 |  |  |  |  |
|  | Ethyl Gly . HCl | 0.10 |  |  |  |  |
| 22 | Cupric naphthenate | 0.64 | 90 | 16.48 | 27.95 | 55.57 |
|  | Ethyl Gly . HCl | 0.97 |  |  |  |  |
|  | Amino Cl Phenol | 0.62 |  |  |  |  |

TABLE 3'

Isomerization of 1, 4-dichlorobutene-2

Reference:

| Exp. | Catalyst | Concentration of catalyst (wt. %) | Reaction temp. (°C.) | Composition (wt. %) 3,4-DCB | cis-1,4-DCB | trans-1,4-DCB |
|---|---|---|---|---|---|---|
| — | Starting material dichlorobutene | — | — | 0.84 | 29.74 | 69.42 |
| 1 | CuCl | 0.50 | 90 | 7.61 | 28.73 | 63.66 |
|  | Triethanolamine | 1.50 |  |  |  |  |
| 2 | CuCl | 0.10 | 90 | 7.93 | 28.69 | 63.38 |
|  | Diethylamine hydrochloride | 0.15 |  |  |  |  |
| 3 | Cupric naphthenate | 1.50 | 90 | 5.52 | 28.61 | 65.87 |
|  | Adiponitrile | 3.10 |  |  |  |  |
| 4 | Cupric naphthenate | 1.50 | 90 | 4.18 | 29.22 | 66.60 |
|  | Nitrobenzene | 3.10 |  |  |  |  |
| 5 | Cupric naphthenate | 1.00 | 90 | 4.92 | 29.21 | 65.87 |
|  | Ethyleneglycol | 1.00 |  |  |  |  |
| 6 | Cupric naphthenate | 0.64 | 90 | 9.47 | 28.69 | 61.84 |
|  | 2,5-dichloroaniline | 0.64 |  |  |  |  |

TABLE 4

Isomerization of 3, 4-dichlorobutene-1

| Exp. | Catalyst | Concentration of catalyst (wt. %) | Reaction temp. (°C.) | Composition (wt. %) 3,4-DCB | cis-1,4-DCB | trans-1,4-DCB |
|---|---|---|---|---|---|---|
| — | Starting material dichlorobutene | — | — | 99.44 | 0.31 | 0.25 |
| 23 | Cupric naphthenate | 0.64 | 90 | 62.00 | 1.13 | 36.87 |
|  | Pip . HCl | 0.97 |  |  |  |  |
| 24 | Cupric acetate | 0.18 | 90 | 72.50 | 0.82 | 26.68 |
|  | Pip . HCl | 0.28 |  |  |  |  |
| 25 | CuCl | 0.10 | 90 | 40.48 | 1.21 | 58.31 |
|  | Ethyl Gly . HCl | 0.20 |  |  |  |  |

TABLE 4-continued

Isomerization of 3, 4-dichlorobutene-1

| Exp. | Catalyst | Concent- ration of catalyst (wt. %) | Reaction temp. (°C.) | Composition (wt. %) 3,4- DCB | cis- 1,4-DCB | trans- 1,4-DCB |
|---|---|---|---|---|---|---|
| 26 | Cupric naphthenate | 0.64 | 90 | 48.85 | 1.13 | 50.02 |
|    | Ethyl Gly . HCl | 0.97 | | | | |
| 27 | Cupric acetate | 0.18 | 90 | 46.12 | 1.15 | 52.73 |
|    | Ethyl Gly . HCl | 0.28 | | | | |
| 28 | Cupric naphthenate | 0.64 | 90 | 44.08 | 1.36 | 54.56 |
|    | Amino Cl Phenol | 0.97 | | | | |
| 29 | CuCl | 0.10 | 90 | 43.27 | 1.34 | 55.39 |
|    | Pip . HCl | 0.15 | | | | |
|    | Ethyl Gly . HCl | 0.10 | | | | |
| 30 | Cupric naphthenate | 0.64 | 90 | 42.19 | 1.29 | 56.52 |
|    | Ethyl Gly . HCl | 0.97 | | | | |
|    | Amino Cl Phenol | 0.62 | | | | |

TABLE 4'

Isomerization of 3, 4-dichlorobutene-1

Reference:

| Exp. | Catalyst | Concent- ration of catalyst (wt. %) | Reaction temp. (°C.) | Compositions (wt. %) 3,4- DCB | cis- 1,4-DCB | trans- |
|---|---|---|---|---|---|---|
| — | Starting material Dichlorobutene | — | — | 99.86 | 0.04 | 0.10 |
| 1 | CuCl | 0.15 | 90 | 93.06 | 0.18 | 6.76 |
|   | Triethanolamine | 0.77 | | | | |
| 2 | Cupric naphthenate | 1.00 | 90 | 83.79 | 0.64 | 15.57 |
|   | Ethyleneglycol | 1.00 | | | | |
| 3 | Cupric naphthenate | 1.00 | 90 | 85.46 | 0.61 | 13.93 |
|   | Adiponitrile | 1.00 | | | | |
| 4 | Cupric naphthenate | 1.00 | 90 | 88.61 | 0.51 | 10.88 |
|   | Nitrobenzene | 1.00 | | | | |

EXAMPLE 31

The process of Example 1 was repeated for the isomerization of 1,4-dichlorobutene-2 except that the amount and type of catalyst employed in several reactions were varied as shown in Table 5 below. The reactions were conducted at 90° C. and analysis of each reaction mixture was achieved by gas chromatography. The results are also shown in Table 5.

TABLE 5

| Exp. | Catalyst | Concent- ration of catalyst (wt. %) | Reaction temp. (°C.) | Composition (wt. %) 3,4- DCB | cis- 1,4-DCB | trans- 1,4-DCB |
|---|---|---|---|---|---|---|
|   | Starting material dichlorobutene | — | — | 0.56 | 7.14 | 92.30 |
| 1 | Cupric naphthenate | 1.5 | 90 | 21.57 | 6.77 | 71.66 |
|   | Diphenyl Gua. | 0.38 | | | | |
| 2 | Cupric acetate | 0.43 | 90 | 17.28 | 6.82 | 75.90 |
|   | Diphenyl Gua. | 0.38 | | | | |
| 3 | Cupric naphthenate | 1.50 | 90 | 20.10 | 6.76 | 73.14 |
|   | Ditolyl Gua. | 0.45 | | | | |
| 4 | Cupric acetate | 0.43 | 90 | 16.43 | 6.82 | 76.75 |
|   | Ditolyl Gua. | 0.45 | | | | |
| 5 | Cupric acetate | 0.43 | 90 | 19.89 | 6.96 | 73.15 |
|   | Amino Cl phenol | 0.60 | | | | |

EXAMPLE 32

The process of Example 1 was repeated for the isomerization of 3, 4-dichlorobutene-1 except that the amount and type of catalyst employed in several reactions were varied as shown in Table 6 below. The reactions were conducted at 90° C. and analysis of each reaction mixture was achieved by gas chromatography. The results are also shown in Table 6.

TABLE 6

| Exp. | Catalyst | Concent- ration of cata- lyst (wt. %) | Re- action temp. (°C.) | Composition (wt. %) 3,4- DCB | cis- 1,4- DCB | trans- 1,4- DCB |
|---|---|---|---|---|---|---|
| — | Starting material dichlorobutene | — | — | 99.95 | 0 | 0.05 |
| 1 | Cupric naphthenate | 1.50 | 90 | 53.44 | 1.15 | 45.41 |
|   | Diphenyl Gua. | 0.38 | | | | |
| 2 | Cupric acetate | 0.43 | 90 | 69.80 | 0.77 | 29.43 |
|   | Diphenyl Gua. | 0.38 | | | | |
| 3 | Cupric naphthenate | 1.50 | 90 | 71.48 | 0.78 | 27.74 |
|   | Ditolyl Gua. | 0.45 | | | | |
| 4 | Cupric acetate | 0.43 | 90 | 67.40 | 0.85 | 31.75 |
|   | Ditolyl Gua. | 0.45 | | | | |
| 5 | CuCl | 0.23 | 90 | 70.53 | 0.80 | 28.67 |
|   | Amino Cl Phenol | 0.60 | | | | |
| 7 | Cupric acetate | 0.43 | 90 | 41.67 | 1.52 | 56.81 |

TABLE 6-continued

| Exp. | Catalyst | Concentration of catalyst (wt. %) | Reaction temp. (°C.) | Composition (wt. %) 3,4-DCB | cis-1,4-DCB | trans-1,4-DCB |
| --- | --- | --- | --- | --- | --- | --- |
| 8 | Amino Cl Phenol<br>CuCl<br>Pip . HCl | 0.60<br>0.23<br>0.30 | 90 | 40.12 | 1.71 | 58.17 |

Having now fully described this invention, it will be apparent to one of ordinary skill in the art that many changes and modifications can be made thereto without departing from the spirit or scope of the invention set forth herein.

What is claimed as new and intended to be secured by Letters Patent is:

1. In an isomerization reaction between 3, 4-dichlorobutene-1 and 1, 4-dichlorobutene-2 in the presence of a catalyst at 80° to 130° C., the improvement comprising:

conducting the isomerization reaction in the presence of a cuprous chloride-1,3-diphenylguanidine or cuprous chloride-di-o-tolylguanidine catalyst or mixtures thereof.

2. The reaction of claim 1, wherein 3, 4-dichlorobutene-1 is isomerized to form 1, 4-dichlorobutene-2.

3. The reaction of claim 1, wherein 1, 4-dichlorobutene-2 is isomerized to form 3, 4-dichlorobutene-1.

4. The reaction of claim 1, wherein the concentration of said copper compound relative to dichlorobutene reactant ranges from 0.05 to 2 wt.%.

5. The reaction of claim 1, wherein the concentration of said 1,3-diphenylguanidine and/or di-o-tolylguanidine relative to dichlorobutene reactant ranges from 0.05 to 4 wt.%.

* * * * *